US006627789B1

(12) United States Patent
VanDenBogart et al.

(10) Patent No.: US 6,627,789 B1
(45) Date of Patent: Sep. 30, 2003

(54) PERSONAL CARE PRODUCT WITH FLUID PARTITIONING

(75) Inventors: Thomas William VanDenBogart, Slinger, WI (US); Amy Michele Achter, Alpharetta, GA (US); Bruce Wilfuhr Achter, Alpharetta, GA (US); Barbara Jean Burns, Appleton, WI (US); Michael Allen Daley, Alpharetta, GA (US); Peter Robert Elliker, Appleton, WI (US); David Martin Jackson, Roswell, GA (US); Nancy Donaldson Kollin, Roswell, GA (US); Gregory Marc Lefkowitz, Atlanta, GA (US); Sylvia Bandy Little, Marietta, GA (US); Tamara Lee Mace, Doraville, GA (US); David Michael Matela, Alpharetta, GA (US); Cynthia Marie Phillips, Neenah, WI (US); David Charles Potts, Dunwoody, GA (US); Lawrence Howell Sawyer, Neenah, WI (US); Michael William Veith, Oshkosh, WI (US); Kevin Wilson Wood, Neenah, WI (US); Dmitry Yavich, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/654,442

(22) Filed: Sep. 1, 2000

Related U.S. Application Data

(60) Provisional application No. 60/159,322, filed on Oct. 14, 1999.

(51) Int. Cl.$^7$ .................................................. A61F 13/15
(52) U.S. Cl. ........................................................ 604/378
(58) Field of Search ................................ 604/367, 378, 604/385.101

(56) References Cited

U.S. PATENT DOCUMENTS

| 2,357,392 A | 9/1944 | Francis, Jr. |
| 3,121,427 A | 2/1964 | Mosier |

(List continued on next page.)

FOREIGN PATENT DOCUMENTS

| EP | 0 202 472 | 11/1986 |
| EP | 0 483 730 | 5/1992 |
| EP | 0 633 009 | 1/1995 |

(List continued on next page.)

OTHER PUBLICATIONS

Chatterjee's Absorbency, Elsevier Science Publishers, B.V. 1985, pp. 36–40.

Article by R.W. Hoyland and R. Field in the Journal *Paper Technology and Industry*, Dec. 1976, p. 291–299.

*Primary Examiner*—Dennis Ruhl
(74) *Attorney, Agent, or Firm*—Steven D. Flack

(57) ABSTRACT

There is provided an intake/retention/transfer material for personal care products like feminine hygiene products, which is a heterogeneous composite containing between 5 and 25 weight percent of a superabsorbent or gelling material and having a density less than 0.17 g/cc. A more particular embodiment contains less than 20 weight percent and a still more particular embodiment contains 15 weight percent or less of a superabsorbent or gelling material. Also provided are absorbent articles which contain the class of intake/transfer materials mentioned above along with additional absorbent layers such that the absorption of a menses simulant provides fluid partitioning of less than 72% of fluid in the intake/transfer/retention composite. Additionally said composite should have retention capacity values greater than 2.7 g/g.

21 Claims, 3 Drawing Sheets

U.S. PATENT DOCUMENTS

| | | | |
|---|---|---|---|
| 3,710,793 A | 1/1973 | Glassman |
| 3,730,184 A | 5/1973 | Mesek |
| 3,765,418 A | 10/1973 | Jones, Sr. |
| 3,855,046 A | 12/1974 | Hansen et al. |
| 3,881,488 A | 5/1975 | Delanty et al. |
| 3,888,257 A | 6/1975 | Cook et al. |
| 3,934,588 A | 1/1976 | Mesek et al. |
| 3,993,820 A | 11/1976 | Repke |
| 4,079,739 A | 3/1978 | Whitehead |
| 4,100,324 A | 7/1978 | Anderson et al. |
| 4,212,302 A | 7/1980 | Karami |
| 4,213,459 A | 7/1980 | Sigl et al. |
| 4,223,677 A | 9/1980 | Anderson |
| 4,333,463 A | 6/1982 | Holtman |
| 4,340,563 A | 7/1982 | Appel et al. |
| 4,341,217 A | 7/1982 | Ferguson et al. |
| 4,375,448 A | 3/1983 | Appel et al. |
| 4,383,376 A | 5/1983 | Numamoto et al. |
| 4,392,908 A | 7/1983 | Dehnel |
| 4,449,979 A | 5/1984 | Holtman |
| 4,494,278 A | 1/1985 | Kroyer et al. |
| 4,560,372 A | 12/1985 | Pieniak |
| 4,585,448 A | 4/1986 | Enloe |
| 4,600,462 A | 7/1986 | Watt |
| 4,639,254 A | 1/1987 | LeGault et al. |
| 4,640,810 A | 2/1987 | Laursen et al. |
| 4,668,566 A | 5/1987 | Braun |
| 4,670,011 A | 6/1987 | Mesek |
| 4,675,209 A | 6/1987 | Pedigrew |
| 4,676,784 A | 6/1987 | Erdman et al. |
| 4,685,915 A | 8/1987 | Hasse et al. |
| 4,699,619 A | 10/1987 | Bernardin |
| 4,701,177 A | 10/1987 | Ellis et al. |
| 4,773,903 A | 9/1988 | Weisman et al. |
| 4,795,453 A | 1/1989 | Wolfe |
| 4,865,596 A | 9/1989 | Weisman et al. |
| 4,908,026 A | 3/1990 | Sukiennik et al. |
| 4,923,454 A | 5/1990 | Seymour et al. |
| 4,950,264 A | 8/1990 | Osborn, III |
| 4,960,477 A | 10/1990 | Mesek |
| 4,973,325 A | 11/1990 | Sherrod et al. |
| 4,994,037 A | 2/1991 | Bernardin |
| 5,009,650 A | 4/1991 | Bernardin |
| 5,030,229 A | 7/1991 | Yang |
| 5,079,074 A | 1/1992 | Steagall et al. |
| 5,087,506 A | 2/1992 | Palumbo |
| 5,092,860 A | 3/1992 | Pigneul |
| 5,104,396 A | 4/1992 | Oatley et al. |
| 5,171,302 A | 12/1992 | Buell |
| 5,176,668 A | 1/1993 | Bernardin |
| 5,197,959 A | 3/1993 | Buell |
| 5,248,309 A | 9/1993 | Serbiak et al. |
| 5,252,374 A | 10/1993 | Larsonneur |
| 5,277,976 A | 1/1994 | Hogle et al. |
| 5,294,478 A | 3/1994 | Wanek et al. |
| 5,300,054 A | 4/1994 | Feist et al. |
| 5,300,055 A | 4/1994 | Buell |
| 5,304,161 A | 4/1994 | Noel et al. |
| 5,330,456 A | 7/1994 | Robinson |
| 5,348,547 A | 9/1994 | Payne et al. |
| 5,363,604 A | 11/1994 | Heyer |
| 5,364,382 A | 11/1994 | Latimer et al. |
| 5,366,451 A | 11/1994 | Levesque |
| 5,382,245 A | 1/1995 | Thompson et al. |
| 5,397,316 A | 3/1995 | LaVon et al. |
| 5,409,768 A | 4/1995 | Dickenson et al. |
| 5,423,786 A | 6/1995 | Fung et al. |
| 5,429,629 A | 7/1995 | Latimer et al. |
| 5,439,458 A | 8/1995 | Noel et al. |
| 5,447,506 A | 9/1995 | Lindquist |
| 5,460,622 A | 10/1995 | Dragoo et al. |
| 5,466,232 A | 11/1995 | Cadieux et al. |
| 5,486,167 A | 1/1996 | Dragoo et al. |
| 5,514,104 A | 5/1996 | Cole et al. |
| 5,514,120 A | 5/1996 | Johnston et al. |
| 5,525,407 A | 6/1996 | Yang |
| 5,527,171 A | 6/1996 | Soerensen |
| H1585 H | 8/1996 | Ahr |
| 5,562,650 A | 10/1996 | Everett et al. |
| 5,589,117 A | 12/1996 | Yang |
| 5,593,399 A | 1/1997 | Tanzer et al. |
| 5,620,430 A | 4/1997 | Bamber |
| 5,637,106 A | 6/1997 | Mitchell et al. |
| 5,641,441 A | 6/1997 | Yang |
| 5,645,542 A | 7/1997 | Anjur et al. |
| 5,647,862 A | 7/1997 | Osborn, III et al. |
| 5,647,863 A | 7/1997 | Hammons et al. |
| 5,669,895 A | 9/1997 | Murakami et al. |
| 5,695,487 A | 12/1997 | Cohen et al. |
| 5,718,699 A | 2/1998 | Brisebois |
| 5,752,945 A | 5/1998 | Mosley et al. |
| 5,797,894 A | 8/1998 | Cadieux et al. |
| 5,817,079 A | 10/1998 | Bergquist et al. |
| 5,820,973 A | 10/1998 | Dodge, II et al. |
| 5,827,253 A | 10/1998 | Young et al. |
| 5,827,254 A | 10/1998 | Trombetta et al. |
| 5,833,678 A * | 11/1998 | Ashton et al. ............... 604/378 |
| 5,843,063 A | 12/1998 | Anderson et al. |
| 5,843,064 A | 12/1998 | Koczab |
| 5,849,000 A * | 12/1998 | Anjur et al. ................. 604/367 |
| 5,866,242 A | 2/1999 | Tan et al. |
| 5,879,343 A | 3/1999 | Dodge, II et al. |
| 5,883,231 A | 3/1999 | Achter et al. |
| 5,916,670 A | 6/1999 | Tan et al. |
| 5,922,163 A | 7/1999 | Helynranta et al. |
| 5,964,743 A | 10/1999 | Abuto et al. |

FOREIGN PATENT DOCUMENTS

| | | |
|---|---|---|
| EP | 0 729 735 | 9/1996 |
| EP | 0 518 291 | 12/1996 |
| EP | 0 640 330 | 5/2000 |
| GB | 2272916 | 6/1994 |
| GB | 2280115 | 1/1995 |
| GB | 2284551 | 6/1995 |
| GB | 2 286 832 | 8/1995 |
| WO | 89/10109 | 11/1989 |
| WO | 90/05808 | 5/1990 |
| WO | 90/11170 | 10/1990 |
| WO | 90/11171 | 10/1990 |
| WO | 90/11181 | 10/1990 |
| WO | 90/11184 | 10/1990 |
| WO | 91/10413 | 7/1991 |
| WO | 93/03699 | 3/1993 |
| WO | 94/02092 | 2/1994 |
| WO | 94/16658 | 8/1994 |
| WO | 98/13003 | 4/1998 |
| WO | 98/22066 | 5/1998 |
| WO | 98/22067 | 5/1998 |
| WO | 98/24392 | 6/1998 |
| WO | 98/24960 | 6/1998 |
| WO | 98/33464 | 8/1998 |
| WO | 98/47456 | 10/1998 |
| WO | 99/32165 | 7/1999 |
| WO | 99/63922 | 12/1999 |
| WO | 99/63923 | 12/1999 |
| WO | 99/63925 | 12/1999 |

* cited by examiner

PERSONAL CARE PRODUCT WITH FLUID PARTITIONING

This application claims the benefit of U.S. Provisional Application No. 60/159,322, filed Oct. 14, 1999.

FIELD OF THE INVENTION

The invention is related to absorbent structures or absorbent systems which are useful in personal care such as feminine care napkins, diapers and training pants, wound care dressings and bandages, and adult incontinence products. More particularly, the invention relates to absorbent systems that must manage complex body fluids like menses and blood and that still remain highly conformable to the body of the wearer.

BACKGROUND OF THE INVENTION

Personal care products typically are made with a top sheet material (also referred to as a cover sheet or liner) an absorbent core and a liquid impervious back sheet. Some may also have a surge layer or other specialized layers between the top sheet and absorbent core.

Such materials, particularly for feminine hygiene product usage, can leak, staining garments and causing constant concern for the wearer. Consumer testing has shown that leakage is the number one concern within the feminine care category. Global consumer market research testing has shown this to be the case in all major regions around the globe.

Currently many other methods are used within the art to attempt to reduce leakage. Examples of product features to reduce leakage include channels to direct fluid longitudinally in the pad, flaps with the intent of creating a physical barrier, topographical features to redirect the fluid, and the like.

There remains a need for a personal care product that reduces leakage in a product by directing the flow of fluid within the pad and locking it up in a way to minimize deformation.

It is an object of the invention to provide an absorbent material which when used in a personal care product can quickly take in fluid, partially retain it in the structure and subsequently transfer it downward away from the user (in the Z-direction). It is a further object of the invention to provide a personal care product in which the product distributes fluid within the structure (in the X-Y plane).

SUMMARY OF THE INVENTION

The objects of the invention are achieved by a personal care product having an intake/retention/transfer material. Such materials may be manufactured by a variety of processes traditionally used to prepare stabilized nonwoven webs including coforming, carding, airlaying, needlepunching, wetlaying, hydroentangling etc. The web may be prepared from a variety of fibers and mixtures of fibers including but not limited to synthetic fibers, natural fibers including hydroentangled pulp, mechanically and chemically softened pulp, staple fibers, slivers, meltblown and spunbond fibers, and the like. Airlaying is the preferred manufacturing process and airlaid nonwoven composites are the preferred intake/retention/transfer material.

In a particular embodiment, the intake/retention/transfer material is a heterogeneous composite containing between 5 and 25 weight percent of a superabsorbent or gelling material and having a density from a positive amount to less than 0.17 g/cc. A more particular embodiment contains less than 20 weight percent and a still more particular embodiment contains 15 weight percent or less of a superabsorbent or gelling material.

Another aspect of this invention relates to absorbent articles which contain the class of intake/transfer/retention materials mentioned above along with additional absorbent layers such that the absorption of a menses simulant provides fluid partitioning of from a positive amount to less than 72% of fluid in the intake/transfer/retention composite. Additionally said composite should have retention capacity values greater than 2.7 g/g. A more preferred embodiment has a fluid partitioning of less than 66% in the intake/transfer/retention composite and a retention capacity value greater than 3 g/g.

DEFINITIONS

Figure 1:
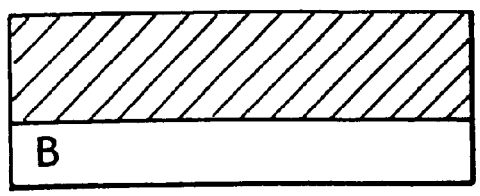
FIGS. 1–5 show various configurations of intake/retention/transfer materials of the invention.

"Disposable" includes being disposed of after a single use and not intended to be washed and reused.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, airlaying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. The fibers may also have shapes such as those described, for example, in U.S. Pat. No. 5,277,976 to Hogle et al. which describes fibers with unconventional shapes.

"Bonded carded web" refers to webs that are made from staple fibers which are sent through a combing or carding unit, which separates or breaks apart and aligns the staple fibers in the machine direction to form a generally machine direction-oriented fibrous nonwoven web.

Pattern bonding is a method wherein heated calender rolls or ultrasonic bonding equipment are used to bond fibers together, usually in a localized bond pattern, though the web can be bonded across its entire surface if so desired. One example of a pattern is the Hansen Pennings or "HP" pattern with about a 30% bond area with about 200 bonds/square inch as taught in U.S. Pat. No. 3,855,046 to Hansen and Pennings. The HP pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern, which produces a 15% bond area. Numerous other bonding patterns exist. Another suitable and well-known bonding method, particularly when using conjugate staple fibers, is through-air bonding, wherein hot air is passed through the web, at least partially melting a component of the web to create bonds.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers may be then bonded to one another using, for example, hot air or a spray adhesive. Airlaying is taught in, for example, U.S. Pat. No. 4,640,810 to Laursen et al.

"Personal care product" means diapers, training pants, absorbent underpants, adult incontinence products, feminine hygiene products, wound care items like bandages, and other articles.

"Feminine hygiene products" means sanitary napkins or pads, tampons and pantyliners.

"Target area" refers to the area or position on a personal care product where an insult is normally delivered by a wearer.

"Composite" is defined as consisting of one or more layers. These may be either similar homogeneous or heterogeneous. It also includes multiple composites which are essentially the same based on structure and surface chemistry.

"Layer" is defined as a smaller sub-set of a composite which may be self-consistent within normal process variation or which may differ in structure or surface chemistry. Alternatively a layer may contain patterns within itself, such as stripes or waves of components. "Layer" when used in the singular may have the dual meaning of singular or plural elements.

Test Method

Material calimer (thickness): The caliper of a material is a measure of thickness and is measured at 0.05 psi (3.5 g/cm$^2$) with a Starret-type bulk tester, in units of millimeters.

Density: The density of the materials is calculated by dividing the weight per unit area of a sample in grams per square meter (gsm) by the material caliper in millimeters (mm) at 0.05 psi (3.5 g/cm$^2$) and multiplying the result by 0.001 to convert the value to grams per cubic centimeter (g/cc). A total of three samples would be evaluated and averaged for the density values.

Absorbency Retained Under Load: Capacity was measured using the dunk, drip and centrifuge capacity test method. Menses simulant was used as the test fluid. Materials were cut using dies into 2.5 inch (6.4 cm) circles. The dry weight and bulk of each sample was then recorded. These were immersed in an isolated bath of excess volume containing simulant for a time of 30 minutes. These materials were then placed on a series of wire screens to allow drainage of excess fluid. Samples were weighed again after the excess fluid was allowed to drip off. The amount of fluid absorbed could be calculated by subtracting these two values. The capacity (in g/g) could be calculated by dividing the amount absorbed by the dry weight of the sample. The sample was then placed on a ⅞ inch (2.2 cm) tall platform having a 2.5 inch (6.4 cm) diameter wire screen upper surface. This platform was then placed in a Sorvall Centrifuge Model RT6000D with arm length radius of 4.5 inches (11.4 cm) and spun at 1200 rpm for 3 minutes. The sample was then weighed. The amount of fluid retained after spinning was calculated by subtracting the dry sample weight from the spun weight. The retention capacity value in g/g was calculated by dividing the amount of fluid retained after spinning by the dry sample weight. Higher values denote better retention while lower values denote less retention.

Flat System Testing Procedure (Modify as Appropriate, Flow Rates, Sample Size):

Purpose: To determine the fluid handling characteristics of various absorbent systems through analysis of stain length, saturation capacity, and fluid partitioning between the system components.

Equipment: Hourglass-shaped acrylic plates approximately 8 inch (30.3 cm) long by 3 inch (7.6 cm) wide at the widest parts and 2.5 inch (6.4 cm) wide at the narrowest point, with a 0.25 inch (6.35 mm) hole in the center, weighing approximately 330 grams; syringes; ⅛ inch (0.32 cm) inside diameter (I.D.) Tygon tubing; Harvard Apparatus Syringe pump; menses simulant as prepared below; laboratory balance (accurate to 0.01 g), Starret-type bulk tester.

Preparation: 1. Cut components to desired shape (currently 1.5 inch (38.1 cm) by 8.0 inch (203.2 cm) for intake/distribution composite; 2.0 inch (50.8 cm) by 8.0 inch (203.2 cm) for transfer delay composite; 2.0 inch (50.8 cm) by 8.0 inch (203.2 cm) for perimeter composite).

2. Weigh and bulk each component and record the values.

3. Assemble the individual components into the desired component system based on the following Testing Sequence description.

Testing Sequence:

1. The appropriate intake/retention/transfer material should be placed over a transfer delay (TDL) composite and these composites placed over a 90% pulp/10% binder, 175 gsm, 0.08 g/cc perimeter composite.

2. The appropriate intake/retention/transfer material should be placed over a 90% pulp/10% binder, 175 gsm, 0.08 g/cc perimeter composite.

3. The appropriate intake/retention/transfer material should be placed over a 90% pulp/10% binder, 175 gsm, 0.17 g/cc perimeter composite.

4. The appropriate intake/retention/transfer material should be placed over a TDL composite and these composites placed over a 80% pulp/10% binder/10% superabsorbent; 175 gsm 0.08 g/cc perimeter composite.

NOTE: In systems with intake/distribution/transfer materials containing a monolayer of SAP, the monolayer should be oriented away from the acrylic plate and toward the TDL unless otherwise noted.

4. Fill the syringes with menses simulant and attach Tygon tubing to syringes.

5. Place syringes in Harvard Apparatus syringe pump.

6. With the open ends of the tubing placed in a beaker, prime tubing by infusing (running) pump until all air is out of tubing and simulant is exiting the tubing at the insult end.

7. Program pump (The flow protocol calls for 30 ml/min for 2 seconds followed by 5 ml/hr for 14 minutes and 58 seconds. This flow sequence in then repeated 4 times for a total of 60 minutes and approximately 9 ml of fluid.).

8. Place the component systems to be tested near the pipette pump, insert the Tygon tubing into the opening in the acrylic plate and place the acrylic plate centered on top of the system.

Repeat for the remaining systems to be tested.

9. Start the pipette pump to begin the insult.
10. At the end of the insult period, remove the tubing and acrylic plates.
11. Take photos of the component system and composites and print.
12. Weigh each composite individually and record the weight. The weight in the upper composite is termed as the fluid partitioning amount in the intake/retention/transfer composite wherein larger amounts of fluid denote less transfer and lower amounts of fluid denote better transfer.
13. Measure and record the stain length for each composite.
14. Enter the data in a spreadsheet for graphing and analysis.

Artificial Menses Preparation: The artificial menses fluid used in the testing was made according to U.S. Pat. No. 5,883,231 from blood and egg white by separating the blood into plasma and red cells and separating the white into thick and thin portions, where "thick" means it has a viscosity after homogenization above about 20 centipoise at 150 $sec^{-1}$, combining the thick egg white with the plasma and thoroughly mixing, and finally adding the red cells and again thoroughly mixing. A more detailed procedure follows:

Blood, in this Example defibrinated swine blood, is separated by centrifuging at 3000 rpm for 30 minutes, though other methods or speeds and times may be used if effective. The plasma is separated and stored separately, the buffy coat removed and discarded and the packed red blood cells stored separately as well. It should be noted that the blood must be treated in some manner so that it may be processed without coagulating. Various methods are known to those skilled in the art, such as defibrinating the blood to remove the clotting fibrous materials, the addition or anti-coagulant chemicals and others. The blood must be non-coagulating in order to be useful and any method which accomplishes this without damaging the plasma and red cells is acceptable.

Jumbo chicken eggs are separated, the yolk and chalazae discarded and the egg white retained. The egg white is separated into thick and thin portions by straining the white through a 1000 micron nylon mesh for about 3 minutes, and the thinner portion discarded. The thick portion of egg white, which is retained on the mesh, is collected and drawn into a 60 cc syringe, which is then placed on a programmable syringe pump and homogenized by expelling and refilling the contents five times. The amount of homogenization is controlled by the syringe pump rate of about 100 ml/min, and the tubing inside diameter of about 0.12 inches. After homogenizing the thick egg white has a viscosity of about 20 centipoise at 150 sect and is then placed in the centrifuge and spun to remove debris and air bubbles at about 3000 rpm for about 10 minutes After centrifuging, the thick, homogenized egg white, which contains ovamucin, is added to a 300 cc FENWAL® Transfer pack container using a syringe. Then 60 cc of the swine plasma is added to the FENWAL® Transfer pack container. The FENWAL® Transfer pack container is clamped, all air bubbles removed, and placed in a Stomacher lab blender where it is blended at normal (or medium) speed for about 2 minutes. The FENWAL® transfer pack container is then removed from the blender, 60 cc of swine red blood cells are added, and the contents mixed by hand kneading for about 2 minutes or until the contents appeared homogenous. A hematocrit of the final mixture should show a red blood cell content of about 30 weight percent and generally should be at least within a range of 28–32 weight percent for artificial menses made according to this Example. The amount of egg white is about 40 weight percent.

The ingredients and equipment used in the preparation of artificial menses are readily available. Below is a listing of sources for the items used, though of course other sources may be used providing they are approximately equivalent.

Blood (swine): Cocalico Biologicals, Inc., 449 Stevens Rd., Reamstown, Pa. 17567, (717) 336-1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

DETAILED DESCRIPTION

The inventors believe that current absorbent products, particularly feminine hygiene products, tend to be over designed, i.e., with leakage occurring long before theoretical capacity is reached. Consumer testing has shown that leakage is the number one unmet need within the feminine care category. Global consumer market research testing shows this to be the case in all major regions around the globe. Another desired attribute for feminine care products is comfort.

An ideal feminine care product would have no leakage and deliver comfort and discretion to the user. Current feminine care pads have relatively high leakage and thus offer only modest protection to the consumer. However, a leak is rather arbitrarily defined in the art and thus consumer perceived leakage is much less. Severe leakage occurs much less frequently.

In the art, a leak is defined as menstrual discharge which stains, contacts or discolors the underwear. All leakage is categorized by three key causes: fluid does not absorb into the product, fluid is absorbed into the product but expelled, or fluid never contacts the product. The specific reasons for this leakage may be expressed further in terms of definitive mechanisms. For instance, fluid may not absorb into the product because it prefers the body. Alternatively, it may not have suitable space for absorption due to localized saturation or low contact area of the product. It may not have a suitable driving force for absorption because the pores do not have the right balance of permeability and capillarity. The interfiber spaces may be partially full of fluid. Fluid may contact the pad and run-off. The fluid may be too viscous for the pores or interfiber spaces are not large enough to allow fluid to pass.

Various product attempts have been defined to reduce leakage. For instance, wings were developed to cover the underwear and thus reduce leakage by reducing the area of the underwear that could be soiled or contacted. Others have defined emboss lines or shaping lines which cause the pad to fold in a predefined manner to concentrate fluid loading in a specific area or to increase the contact area of the pad with the body.

Others have attempted to reduce leakage by focusing on side or edge leakage presumably caused by compression of the pad by the legs thereby reducing the contact area of the target zone. These product designs have focused on keeping absorbed fluid away from the edges of the product and directing it toward the center. In many cases this is a function not only of the assembly of materials of different size and shape but also their ability to conform to and contact the body in predefined ways. In all cases, the material systems and their structure in a specific product design dramatically impact leakage. In the field of material systems design, leakage is a function of materials shaping and conformability as well as intake, distribution, retention and transfer.

Another cause of leakage is severe deformation of the product, which is also referred to as bunching. When a product loses it shape and bunches, the probability of side leakage is greatly increased. As a product becomes saturated with fluid, material resiliency is reduced thus increasing the probability of bunching and so the probability of leakage. One way to reduce this method of leakage is to control the fluid and allocate it within the product in a way that minimizes the probability of bunching, which causes leakage. Those skilled in the art know that bunching and leakage may be reduced by keeping fluid in the center of the pad and in the upper zones above the centerline of the pad. Alternatively, stiffer materials may be incorporated in the center of the pad to reduce bunching. Since stiffness of composites increases upon saturation, the overall fluid saturation of stiffer composites may be reduced and fluid transferred to lower layers of the material. It should be noted, however, that stiffness and resiliency of materials are generally inversely related. The invention designs described herein provide control of the fluid in a way that allows higher fluid transfer than conventional systems such as KOTEX® feminine products, and still presumably permits bunching to be minimized. Taught herein is a material which should increase retention of fluid in the absorbent in the upper composites next to the liner and for specified structures can transfer fluid into sub-absorbent layers potentially reducing leakage, improving dryness and comfort while still minimizing bunching and twisting.

This invention focuses on the development of composites that control the intake/retention and transfer of fluid within a system of composites using superabsorbent containing materials both homogeneous and heterogeneous comprised of specific ranges of composition bulk, density, basis weight and superabsorbent placement.

A particularly preferred embodiment of this invention is a heterogeneous composite wherein the superabsorbent is contained within the lowest layer, with a preference of less than 35% of thickness of the intake/retention/transfer composite. It is this lowest layer which is in contact with a second absorbent material subjacent to it. At composite densities less than 0.12 g/cc and superabsorbent loading less than 30%, the material is designed to quickly absorb and distribute in the upper layers. As the fluid moves down through the composite it interfaces with the lower superabsorbent-containing element of the core. Menses tends to distribute along the interface point between the zone containing superabsorbent and the zone not containing superabsorbent, initially slowing down the transfer in the Z direction and increasing distribution along the length of the product. The superabsorbent then begins to lock the fluid in the lower portion of the material. As the composite superabsorbent swells, it expands the lower structure decreasing the density and providing an increased driving force for transfer due to capillarity differences between the upper and lower absorbent. For composites of this type at densities less than 0.12 g/cc the superabsorbent will expand sufficiently such that the capillarity is decreased considerably. Alternative embodiments are also obvious, such as incorporating stiff and/or resilient fibers such as curly or crosslinked pulps and polyesters with superabsorbent. These stiff fibers will allow for increased SAP swelling thus promoting increased capacity utilization of the superabsorbent as well as increasing capillary gradient and thus opportunities for fluid transfer.

Another preferred embodiment of this invention is a heterogeneous structure wherein the superabsorbent is contained within the lowest layer of the intake/retention/transfer composite wherein the composite density is greater than 0.12 g/cc and superabsorbent loading less than 30%. These types of composites perform similarly to those of lower density with the exception that the superabsorbent does not tend to swell as much at these higher densities due to increased resistance against swelling. This increased resistance is presumably related to an increase in inter-fiber bonding at higher densities. Therefore composites of this type tend to increase wicking and distribution and decrease transfer (partitioning more fluid in the upper absorbent) compared to lower density composites of similar composition in similar absorbent systems.

Homogeneous composites containing superabsorbent tend to have similar transfer and retention properties as their heterogeneous counterparts but tend to distribute the fluid less.

In a particular embodiment, the intake/retention/transfer material is a homogeneous or heterogeneous composite containing between 5 and 25 weight percent of a superabsorbent or gelling material and having a density from a positive amount to less than 0.17 g/cc. A more particular embodiment contains less than 20 weight percent and a still more particular embodiment contains 15 weight percent or less of a superabsorbent or gelling material.

Another aspect of this invention relates to absorbent articles which contain the class of intake/transfer materials mentioned above along with additional absorbent layers such that the absorption of a menses simulant provides fluid partitioning of essentially less than 72% of fluid in the intake/transfer/retention composite. Additionally the composite should have retention capacity values greater than 2.7 g/g. A more preferred embodiment has a fluid partitioning of less than 66% in the intake/transfer/retention composite and a retention capacity value greater than 3 g/g.

The intake/retention/transfer materials of this invention may be made from a variety of processes traditionally used to prepare stabilized nonwoven webs including coforming, carding, airlaying, needlepunching, wetlaying, hydroentangling etc., though the airlaying process is preferred. The nonwoven web may be prepared from a variety of fibers and mixtures of fibers including but not limited to synthetic fibers, natural fibers including hydroentangled pulp, mechanically and chemically softened pulp, staple fibers, slivers, meltblown and spunbond fibers, and the like.

In a particular embodiment, the intake/retention/transfer material is an airlaid structure containing less than 25 weight percent of superabsorbent or gelling material. A more particular embodiment contains less than 20 weight percent and a still more particular embodiment contains 15 weight percent or less of superabsorbent or gelling material.

Superabsorbents that are useful in the present inventions can be chosen from classes based on chemical structure as well as physical form. These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly(vinyl pyrrollidone), and poly(-vinyl alcohol). The superabsorbents may range in swelling rate from slow to fast. The superabsorbents may be in the form of foams, macroporous or microporous particles or fibers, particles or fibers with fibrous or particulate coatings or morphology. The superabsorbents may be in the shape of ribbons, particles, fibers, sheets or films. Superabsorbents may be in various length and diameter sizes and distributions. The superabsorbents may be in various degrees of neutralization. Counter-ions are typically Li, Na, K, Ca.

Materials of this invention may include superabsorbents of the types mentioned above. An exemplary superabsorbent was obtained from The Dow Chemical Company and is recognized as AFA-173-60B. An Example of these types of superabsorbents may be obtained from Stockhausen, Inc and is designated FAVOR® SXM 880. An example of fibrous superabsorbents may be obtained from Camelot Technologies, Ltd., of High River, Alberta, Canada and is designated FIBERDRI® 1241. Another Example included in these types of superabsorbents is obtained from Chemtall Inc. or Riceboro, Ga., and is designated FLOSORB 60 LADY®, also known as LADYSORB 60®. Examples of superabsorbents with fibrous or particulate coatings are microcrystalline cellulose coated on FAVOR® 880 and cellulose fiber coated FAVOR® 880. These are described in U.S. Provisional Patent Application No. 60/129,774. Additional types of superabsorbents not listed here which are commonly available and known to those skilled in the art can also be useful in the present inventions.

Binders typically used in these structures help provide mechanical integrity and stabilization. Binders include fiber, liquid or other binder means which may thermally activated. Preferred fibers for inclusion are those having a relative melting point such as polyolefin fibers. Lower melting point polymers provide the ability to bond the fabric together at fiber crossover points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a glass transition temperature less than about 175 C. It should be noted that the texture of the absorbent web could be modified from soft to stiff through selection of the glass transition temperature of the polymer. Exemplary binder fibers include conjugate fibers of polyolefins, polyamides and polyesters. Three suitable binder fibers are sheath core conjugate fibers available from KoSa Inc. (Charlotte, N.C.) under the designation T-255 (Merge 34821 A) and T-256 or Copolyester designation, though many suitable binder fibers are known to those skilled in the art, and are available by many manufacturers such as Chisso and Fibervisions LLC of Wilmington, Del. KoSa has developed a suitable co-polyester binder fiber as a sheath core application and is known by designation T254 (low melt COPET). A suitable liquid binder is KYMENE® 557LX available from Hercules Co. of Wilmington, Del. Other suitable liquid binders include ethylene vinyl acetate emulsion polymers sold by National Starch and Chemical Company (Bridgewater, N.J.) under the tradename DUR-O-SET® ELITE® series (including ELITE®) 33 and ELITE® 22). Air Products Polymers and Chemicals sells other suitable binder fibers under the name AIRFLEX®.

Synthetic fibers include those made from polyamides, polyesters, rayon, acrylics, superabsorbents, TENCEL® regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A liner low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Many other polyolefins are also available.

Particularly preferred materials for this application include polyesters, which may range in size or denier from 3 to 25 denier, and having various cross-sections including round, pentalobal, helical crimped, etc. Such fibers have been developed by KoSa, Inc. with a durably wettable finish and are known by designation of fiber denier followed by polymer type and cross section. Examples would include 8 dpf, T-224 (High Void); 8 dpf, T-224 (trilobal); 15 dpf T-224 (round); 10 dpf T-224 (round); 6 dpf T-224 (round) and 3 dpf T-224 (round).

Natural fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes, maleic anhydride, non-methylolated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation. Suitable rayon fibers are 1.5 denier Merge 18453 fibers from Tencel Incorporated of Axis, Ala.

In one embodiment, the superabsorbent is relatively homogeneously distributed within a nonwoven web. The remainder of the web may contain synthetics, pulps or binders as described above. The superabsorbent medium or gelling agents may be captured or contained within the web chemically, physically or mechanically. Mechanical means would involve tailoring the interfiber spacing or shape such that superabsorbent particles are primarily entrapped within the structure. This can be achieved by adjusting interfiber spacing, on the order of the size of the particles, or could include interfiber spacing larger than the superabsorbent wherein the tortuosity of the interfiber spacing is increased. Physical or chemical means could involve the use of adhesive such as emulsions of latex or others to retain the superabsorbent within the structure and conjugate binder fibers or bonding fibers may also be used. Other means of attachment may include a chemical reaction with the fibrous matrix or alternate media. In addition, electret treating has been used to modify the charges on superabsorbent type materials and the fibrous substrate, thereby permitting attachment.

Particular embodiments of the application combine the use of synthetic fibers with superabsorbent to provide resiliency and enhance the fluid swelling capacity of the superabsorbent through reduction of localized resistance to swelling due to impedance by the fibrous matrix.

A preferred embodiment consists of 5–25 weight percent superabsorbent particle or fiber, 5–15 weight percent binder fiber, 0–40 weight percent synthetic, and pulp.

The superabsorbent may also be heterogeneously distributed within the rest of the nonwoven structure to obtain layered structures wherein a multi-layer, multifunctional composite is created. Superabsorbent may, for example, be distributed only in the bottom layer.

One embodiment would be a structure having two layers, A and B, as shown in FIG. 1, wherein layer A would have 5–15 weight percent binder fiber, 0–40 weight percent synthetic fiber, and pulp. Layer B would consist of 5–15 weight percent binder fiber, 0–40 weight percent synthetic fiber and less than 60 weight percent superabsorbent or gelling material, and pulp. This yields a structure having less than 25 weight percent superabsorbent for the overall structure. Layers A and B can also be made over a range of basis weights and densities to provide for the optimum intake/retention/transfer of a specific viscoelastic fluid or for a viscoelastic fluid with a broad range of fluid characteristics. The overall composite basis weight can range from 40 gsm to 400 gsm while ranges of basis weight from 125 to 300 gsm are preferred. Density ranges for these materials typically span a range of 0.03 to 0.24 g/cc with a more preferred range of 0.06 to 0.14 g/cc. Furthermore, it is conceivable that the density could vary throughout the material such that the upper material has a lower density than the lower material.

Figure 2:
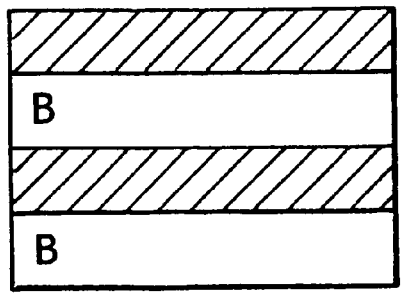

An alternate embodiment would include multiple layered components within the same structure as shown in FIG. 2.

Figure 3:
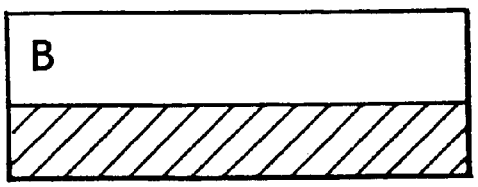

Superabsorbent may be distributed only in the top layers (FIG. 3) or may be distributed in the middle layers of the material.

Figure 4:
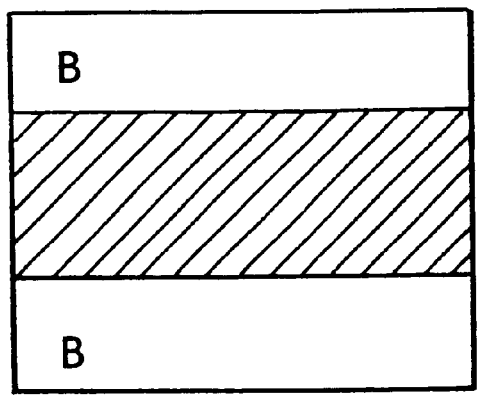
Figure 5:
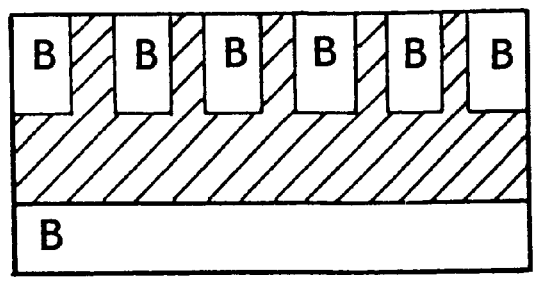

Multiple layers may be created wherein superabsorbent is primarily interspersed within or between layers of the material. Superabsorbent may also be layered or interspersed within the depth of the product as well as shown in FIG. 4. Superabsorbent may also be distributed heterogeneously within layers. Superabsorbent may also be dispersed within the plane of a material as shown in FIG. 5.

In a particular embodiment, the intake/retention/transfer material is a heterogeneous composite containing between 5 and 25 weight percent of a superabsorbent or gelling material and having a density less than 0.17 g/cc. A more particular embodiment contains less than 20 weight percent and a still more particular embodiment contains 15 weight percent or less of a superabsorbent or gelling material.

Another aspect of this invention relates to absorbent articles which contain the class of intake/transfer materials mentioned above along with additional absorbent layers such that the absorption of a menses simulant provides fluid partitioning of less than 72% of fluid in the intake/transfer/retention composite. Additionally said composite should have retention capacity values essentially greater than 2.7 g/g. A more preferred embodiment has a fluid partitioning of less than 66% in the intake/transfer/retention composite and a retention capacity value greater than 3 g/g.

EXAMPLES

Intake/Retention/Transfer Composites

Example 1

Composite A is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 2

Composite A is a bilayer airlaid which has an overall basis weight of 205 gsm with a density of 0.105 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 3

Composite A is a homogeneous airlaid composite which has an overall basis weight of 269 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot).

Example 4

Composite A is a bilayer airlaid which has an overall basis weight of 198 gsm with a density of 0.085 g/cc and is composed of 80% Southern Softwood (NB416), 10% 2.1 dpf binder fiber (T-255) and 10% superabsorbent particle (SAP)—FAVOR® 880 (Stockhausen). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 5

Composite A is a bilayer airlaid which has an overall basis weight of 247 gsm with a density of 0.15 g/cc and is composed of 80% Southern Softwood (NB416), 10% 2.1 dpf binder fiber (T-255) and 10% superabsorbent particle (SAP)—FAVOR® 880 (Stockhausen). Upper Layer—

195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 6

Composite A is a bilayer airlaid which has an overall basis weight of 258 gsm with a density of 0.185 g/cc and is composed of 80% Southern Softwood (NB416), 10% 2.1 dpf binder fiber (T-255) and 10% superabsorbent particle (SAP)—FLOSORB 60 LADY®. Upper Layer—195 gsm consisting of 90% Southern Softwood (NB416) and 10% 2.1 dpf binder fiber (T-255).

Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 7

Composite A is a bilayer airlaid which has an overall basis weight of 186 gsm with a density of 0.11 g/cc and is composed of 80% Southern Softwood (NB416), 10% 2.1 dpf binder fiber (T-255) and 10% superabsorbent particle (SAP)—Coated FAVOR® 880. Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 8

Same as Composite 1 Except Evaluated Using Test Sequence 2 for Flat Systems Testing Procedure Composite A is a bilayer airlaid which has an overall basis weight of 260 gsm with a density of 0.14 g/cc and is composed of 80% Southern Softwood (NB416), 10% 2.1 dpf binder fiber T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 9

Same as Composite 2 Except Evaluated Using Test Sequence 2 for Flat Systems Testing Procedure Composite A is a bilayer airlaid which has an overall basis weight of 205 gsm with a density of 0.105 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 10

Same as Composite 1 Except Evaluated Using Test Sequence 3 for Flat Systems Testing Procedure Composite A is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 11

Same as Composite 3 Except Evaluated Using Test Sequence 2 for Flat Systems Testing Procedure Composite A is a bilayer airlaid which has an overall basis weight of 205 gsm with a density of 0.105 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 12

Same as Composite 3 Except Evaluated Using Test Sequence 3 for Flat Systems Testing Procedure Composite A is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Example 13

Same as Composite 3 Except Evaluated Using Test Sequence 3 for Flat Systems Testing Procedure Composite A is a bilayer airlaid which has an overall basis weight of 205 gsm with a density of 0.105 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255).

Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Product Examples

Figure 6:
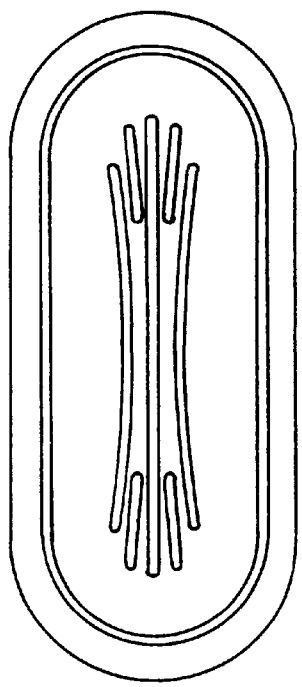
FIGS. 6 and 7 show arrangements of materials for feminine hygiene pads incorporating the intake/retention/transfer materials of the invention.
Figure 7:
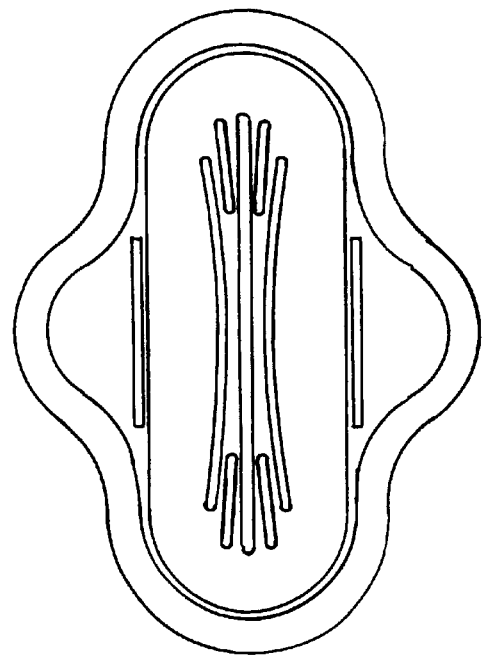
Figure 8:
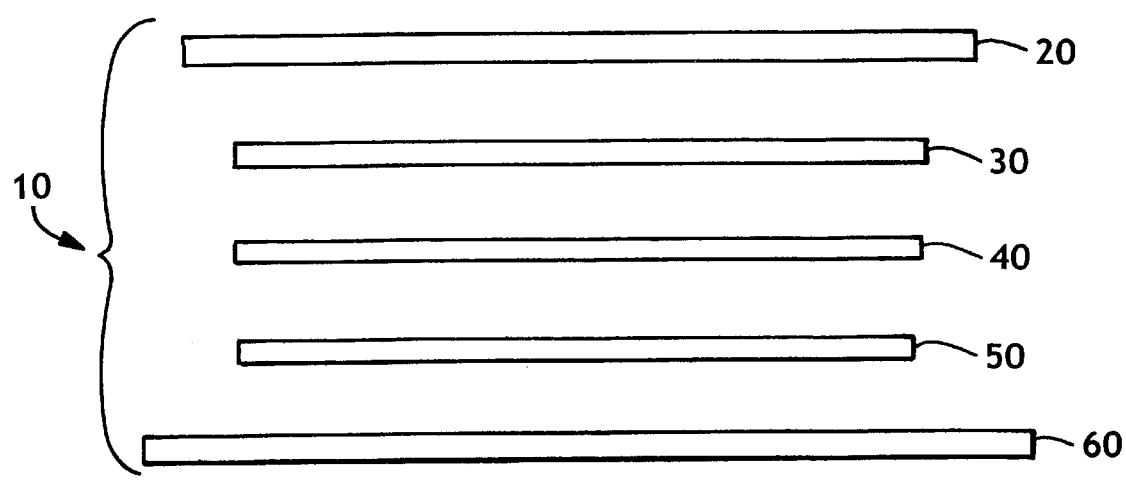
FIG. 8 shows an exploded cross section of a personal care product incorporating the intake/retention/transfer materials of the invention.

Examples apply but are not limited to FIGS. 6 and 7. A cross sectional view of a personal care product incorporating the intake/retention/transfer materials of the invention is further illustrated in FIG. 8. In FIG. 8, an absorbent article exploded cross section is shown 10, having a liner or topsheet 20, an intake composite (intake/retention/transfer material) 30 such as for example, those illustrated in FIGS. 1–5, a transfer delay composite 40, a shaping composite 50 (storage area/second or lower absorbent), and a baffle 60. It should be recognized that certain embodiments do not include the optional transfer delay layer.

Example 14 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 TiO$_2$ (50% concentrate) and point bonded using Hansen & Pennings (HP) pattern. Web was topically treated to 0.3% AHCOVEL® Base N62 (ICI Surfactants, Delaware).

Intake Composite Composite is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)

Construction Adhesive National Starch & Chemical (EASYMELT® 34-5610)

Example 15 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 TiO$_2$ (50% concentrate) and point bonded using Hansen & Pennings (HP) pattern. Web was topically treated to 0.3% AHCOVEL® Base N62 (ICI Surfactants, Delaware).

Intake Layer Composite is a bilayer airlaid which has an overall basis weight of 205 gsm with a density of 0.105 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL© Base N62 62 (ICI Chemicals, Delaware)

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)

Construction Adhesive National Starch & Chemical (EASYMELT® 34-5610)

Example 16 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 TiO$_2$ (50% concentrate) and point bonded using Hansen & Pennings (HP) pattern. Web was topically treated to 0.3% AHCOVEL® Base N62 (ICI Surfactants, Delaware).

Intake Composite Composite is a homogeneous airlaid composite which has an overall basis weight of 269 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)

Construction Adhesive National Starch & Chemical (EASYMELT® 34-5610)

Example 17 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 TiO$_2$ (50% concentrate) and point bonded using Hansen & Pennings (HP) pattern. Web was topically treated to 0.3% AHCOVEL® Base N62 (ICI Surfactants, Delaware).

Intake Composite Composite is a bilayer airlaid which has an overall basis weight of 198 gsm with a density of 0.085 g/cc and is composed of 80% Southern Softwood (NB416), 10% 2.1 dpf binder fiber (T-255) and 10% superabsorbent particle (SAP)—FAVOR® 880 (Stockhausen). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)

Construction Adhesive National Starch & Chemical (EASYMELT® 34-5610)

Example 18 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 TiO$_2$ (50% concentrate) and point bonded using Hansen & Pennings (HP) pattern. Web was topically treated to 0.3% AHCOVEL® Base N62 (ICI Surfactants, Delaware).

Intake Composite Composite A is a bilayer airlaid which has an overall basis weight of 247 gsm with a density of 0.15 g/cc and is composed of 80% Southern Softwood (NB416), 10% 2.1 dpf binder fiber (T-255) and 10% superabsorbent particle (SAP)—FAVORS® 880 (Stockhausen). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)
Construction Adhesive National Starch & Chemical (EASYMELT® 34-5610)

Example 19 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 $TiO_2$ (50% concentrate) and point bonded using Hansen & Pennings (HP) pattern. Web was topically treated to 0.3% AHCOVEL® Base N62 (ICI Surfactants, Delaware).

Intake Composite Composite A is a bilayer airlaid which has an overall basis weight of 258 gsm with a density of 0.185 g/cc and is composed of 80% Southern Softwood (NB416), 10% 2.1 dpf binder fiber (T-255) and 10% superabsorbent particle (SAP)—FLOSORB 60 LADY®. Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware).

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)
Construction Adhesive National Starch & Chemical (EASYMELT® 34-5610)

Example 20 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 $TiO_2$ (50% concentrate) and point bonded using Hansen & Pennings (HP) pattern. Web was topically treated to 0.3% AHCOVEL® Base N62 (ICI Surfactants, Delaware).

Intake Composite Composite A is a bilayer airlaid which has an overall basis weight of 186 gsm with a density of 0.11 g/cc and is composed of 80% Southern Softwood (NB416), 10% 2.1 dpf binder fiber (T-255) and 10% superabsorbent particle (SAP)—Coated FAVOR® 880. Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)
Construction Adhesive National Starch & Chemical (EASYMELT® 34-5610)

Example 21 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 $TiO_2$ (50% concentrate) and point bonded using Hansen & Pennings (HP) pattern. Web was topically treated to 0.3% AHCOVEL® Base N62 (ICI Surfactants, Delaware).

Intake Composite Composite A is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Shaping Composite 175 gsm, 0.08 g/cc composed of 90% Southern Softwood (NB416) and 10% 2.1 dpf binder fiber (T-255).

Baffle 1.25 mil polyethylene film, rose colored (Huntsman)
Construction Adhesive National Starch & Chemical (EASYMELT® 34-5610)

Example 22 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 $TiO_2$ (50% concentrate) and point bonded using Hansen & Pennings (HP) pattern. Web was topically treated to 0.3% AHCOVEL® Base N62 (ICI Surfactants, Delaware).

Intake Composite Composite A is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Shaping Composite 175 gsm, 0.17 g/cc composed of 90% Southern Softwood (NB416) and 10% 2.1 dpf binder fiber (T-255).

Baffle 1.25 mil polyethylene film, rose colored (Huntsman)
Construction Adhesive National Starch & Chemical (EASYMELT® 34-5610)

Example 23 is an absorbent article for managing viscoelastic fluids containing:

Liner or Topsheet 3.5 dpf, 0.6 osy (20.3 gsm) Polypropylene Spunbond (92% Union Carbide E5D47 PP+8% AMPACET® 41438 $TiO_2$ (50% concentrate) and point bonded using Hansen & Pennings (HP) pattern. Web was topically treated to 0.3% AHCOVEL® Base N62 (ICI Surfactants, Delaware).

Intake Composite Composite is a bilayer airlaid which has an overall basis weight of 260 gsm with a density of 0.14 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 80% Southern Softwood (NB416), 10% 2.1 dpf binder fiber (T-255) and 10% superabsorbent fiber (SAF)—FIBERDRI® 1241 (Camelot).

Baffle 1.25 mil polyethylene film, rose colored (Huntsman)
Construction Adhesive National Starch & Chemical (EASYMELT® 34-5610)

Example 24 is an absorbent article for managing viscoelastic fluids containing:

Liner or Topsheet Apertured film laminate described in PCT WO 96/40513. 3.5 dpf, 0.6 osy (20.3 gsm) Polypropylene Spunbond (92% Union Carbide E5D47 PP+8% AMPACET® 41438 $TiO_2$ (50% concentrate) and point bonded using Hansen & Pennings (HP) pattern. Web was topically treated to 0.3% AHCOVEL® Base N62 (ICI Surfactants, Delaware).

Intake Composite Composite is a bilayer airlaid which has an overall basis weight of 205 gsm with a density of 0.105 g/cc and is composed of 80% Southern Softwood (NB416), 10% 2.1 dpf binder fiber (T-255) and 10% superabsorbent fiber (SAF)—FIBERDRI® 1241 (Camelot). Upper Layer—195 gsm consisting of 90% Southern Softwood (NB416) and 10% 2.1 dpf binder fiber (T-255). Lower Layer—65 gsm consisting of 50% Southern Softwood (NB416), 10% 2.1 dpf binder fiber (T-255) and 40% superabsorbent fiber (SAF)—FIBERDRI® 1241 (Camelot).

Transfer Delay composite 2.8 dpf, 0.8 osy (27.1 gsm) polypropylene spunbond topically treated with 0.3% AHCOVEL® Base N62 62 (ICI Chemicals, Delaware)

Shaping Composite 175 gsm, 0.08 g/cc composed of 80% Southern Softwood (NB416), 10% 2.1 dpf binder fiber (T-255) and 10% superabsorbent fiber (SAF)—FIBERDRI® 1241 (Camelot).

Baffle 1.25 mil polyethylene film
Construction Adhesive National Starch & Chemical (EASYMELT® 34-5610)

Comparative Samples

Comparative Sample 1

Always® Overnight Maxi with Wings Universal Product Code (UPC) 37000 30165.

Comparative Sample 2

KOTEX® Ultrathin Maxi UPC 36000 03014.

Comparative Sample 3

Composite A is a homogeneous airlaid which has an overall basis weight of 262 gsm with a density of 0.14 g/cc and is composed of 90% Southern Softwood (NB416) and 10% 2.1 dpf binder fiber (T-255).

Comparative Sample 4

Composite A is a homogeneous airlaid which has an overall basis weight of 252 gsm with a density of 0.09 g/cc and is composed of 90% Southern Softwood (NB416) and 10% 2.1 dpf binder fiber (T-255).

The Table summarizes the material Examples and Comparative Samples as well as the test results from the flat systems test and the absorbency under load tests. The Table also includes composite composition and density. Since absorbent sub-composites which are in liquid communication with the top (intake/retention/transfer) composite are required for the flat systems test, they're description is also included. In particular, the composition, basis weight, and density are described for the perimeter or shaping composite and it is noted whether or not a transfer delay composite is utilized.

Examples 1, 5, and 6 refer to heterogeneous composites which are approximately 250 gsm basis weight and densities between 0.14 and 0.185 g/cc. These composites contain different superabsorbents in the bottom layer. These superabsorbents include fiber forms such as FIBERDRI® 1241 (C1241) and particulate forms such as FAVOR® 880 and FLOSORB 60 LADY®. One notes from the fluid allocation or fluid partitioning values that the amount of fluid in the top layer or intake/retention/transfer composite as measured using the flat systems test is approximately 64 to 65%. The stain lengths in the top layer are also similar ranging from 92 to 98 mm. From Examples 1 and 5, one notes that different superabsorbents behave very similarly in these composites. It is difficult to draw the same conclusions from Example 6 since its density is much higher than the other composites. In fact, one may find that such a superabsorbent demonstrates increased transfer at densities near 0.14. If so, this effect could be related to the gel strength and form of the superabsorbent. One observes that the retention capacity values for examples 1, 5, and 6 are similar with Example 6 demonstrating the highest value. Comparing samples 1, 5, and 6 to Comparative Sample 3, a material at similar density and basis weight but with no superabsorbent, one notes that these materials have relatively the same fluid partitioning values and stain length in the top composite. Comparing the fluid retention values, one observes that the retention capacity for Comparative Sample 3 is 2.4 compared to the range of 3.60 to 3.95 for examples 1, 5, and 6. Comparing Example 1 to Example 3, one can compare the effect of superabsorbent placement within the structure: homogeneous versus heterogeneous. We observe that homogeneous composites have higher fluid transfer within a monolayer than heterogeneous composites and thus less fluid in the intake/transfer/retention composite. We also observe that the retention capacity values for homogeneous composites are higher than heterogeneous monolayer composites at equivalent superabsorbent concentrations. Comparing Example 1 to Example 8, one can observe the effect that a transfer delay composite has on fluid partitioning and stain length. From these values, one notes that the numbers are similar suggesting that the presence of a transfer delay composite has little impact when used in combination with these absorbent composites. Comparing Example 10 with Example 1, the impact of driving force or difference in capillary tension between upper and lower composites on fluid allocation and stain length and retention capacity values may be observed. One notes that larger positive driving forces improve transfer resulting in smaller stain lengths and less fluid in the top composite. Comparing Examples, 1 and 12, the effects of the presence of superabsorbent in the bottom or shaping composite may be observed. One notes that fluid allocation and stain length are very similar. Looking at Examples, 2, 4, and 7, one can observe the effects of different superabsorbents at approximately 200 gsm basis weight and densities between 0.14 and 0.185 g/cc, one observes that the three superabsorbents behave quite differently with the FAVOR® 880 having the least transfer (most fluid in intake/retention/transfer composite) and Coated FAVOR® 880 having the most transfer (least fluid in intake/retention/transfer composite). Comparing these Examples to Comparative Sample 4 (CS4), a Comparative Sample at slightly higher basis weight which contains no superabsorbent, one notes that the fluid retention is approximately 73% compared to a range of 42 to 58% for examples 2, 4, and 7. Some of this difference may be attributed to difference in basis weight between the Comparative Samples and the Examples but more probably the effect is due to the interaction with the fibrous structure at these lower densities. More specifically it is believed that at composite densities less than 0.12 g/cc and superabsorbent loading less than 30%, the material quickly absorbs and distributes fluid in the upper layers. As the fluid moves down through the composite it interfaces with the lower superabsorbent containing layer of the core. Menses tends to distribute along the interface point between the layer containing superabsorbent and the layer not containing superabsorbent, initially slowing down the transfer in the Z direction and increasing distribution along the length of the product. The superabsorbent then begins to lock the fluid in the lower portion of the material. As the composite superabsorbent swells, it expands the lower structure decreasing the density and providing an increased driving force due to capillarity differences between the upper and lower absorbent. For composites of this type at densities less than 0.12 g/cc the superabsorbent will expand sufficiently that the capillarity is decreased considerably. Comparing Examples 2, 4, and 7 to Comparative Sample 3 one notes that the retention values of the superabsorbent containing structures are much higher. Comparing sample CS3 to CS4, one notes that the amount of fluid in the top composite for CS4 is higher than that for CS3 presumably due to the higher void volume. The amount of fluid retained in the upper layer for examples 2, 4, and 7 is lower than that in Examples 1, 5, and 6. CS1 and CS2 were placed in the study to illustrate how commercial materials behave. One notes that the upper composites for both materials have very low retention capacity values. The fluid allocation in the top composite is very different for these products with 84% for CS1 and about 23% for CS2. The stain lengths for these materials are much higher than the Examples herein. Thus compared to commercial products CS1 and CS2, these materials offer the ability for fluid distribution with improved retention while demonstrating intermediate amounts of fluid transfer based on fluid partitioning values.

As will be appreciated by those skilled in the art, changes and variations to the invention are considered to be within the ability of those skilled in the art. Such changes and variations are intended by the inventors to be within the scope of the invention.

What is claimed is:

1. A material for use in a personal care product comprising a liner, an intake/retention/transfer composite and a storage layer, said composite having between more than 6 and 25 weight percent superabsorbent, between 5 and 15 weight percent binder, between 0 and 40 weight percent synthetic fiber, and pulp, said composite having a density less than 0.17 g/cc, said material demonstrating fluid partitioning such that less than 72 percent of a menses simulant insult remains in said composite as measured by weight percentages of simulant in accordance with a flat system testing procedure, and further wherein said composite has a retention capacity of at least 2.7 g/g.

2. The material of claim 1 wherein said composite comprises between more than 6 and 20 weight percent superabsorbent.

3. The material of claim 2 wherein said composite comprises between more than 6 and 15 weight percent superabsorbent.

4. The material of claim 2 comprising between 10 and 20 weight percent superabsorbent.

5. The material of claim 1 further comprising a transfer delay composite.

6. A personal care product selected from the group consisting of diapers, training pants, absorbent underpants, adult incontinence products and feminine hygiene products comprising the material of claim 5.

7. The material of claim 5 wherein said transfer delay layer is a spunbond web.

8. The material of claim 7 wherein said spunbond web is made from polyolefin.

9. The material of claim 1 wherein said superabsorbent is distributed in said composite such that said composite comprises a first layer and a second subjacent layer, said first layer having essentially no superabsorbent, said first layer having between 5 and 15 weight percent of the layer being binder, said first layer having between 5 and 40 weight percent of the layer being synthetic fiber, and pulp, and said second subjacent layer having less than 60 weight percent of the layer being superabsorbent, said second subjacent layer having between 5 and 15 weight percent of the layer being binder, and said second subjacent layer having between 5 and 40 weight percent of the layer being synthetic fiber, and pulp.

10. The material of claim 1 wherein said composite has a density between 0.12 and 0.17 g/cc.

11. The material of claim 1 wherein said composite has a density of less than 0.12 g/cc.

12. The material of claim 11 wherein said composite has less than 30 percent superabsorbent.

13. A personal care product selected from the group consisting of diapers, training pants, absorbent underpants, adult incontinence products, wound care products, and feminine hygiene products comprising the material of claim 1.

14. The product of claim 13 wherein said personal care product is a feminine hygiene product.

15. The material of claim 1 wherein said liner is an selected from the group consisting of spunbond webs and apertured film and laminates thereof.

16. The material of claim 1 further comprising a baffle.

17. The material of claim 16 wherein said baffle is a film.

18. The material of claim 1 wherein said storage layer comprises pulp and binder fiber.

19. The material of claim 18, wherein said storage layer further comprises superabsorbent.

20. The material of claim 1 wherein said superabsorbent is homogeneously distributed in said composite.

21. A material for use in a personal care product comprising a polypropylene spunbond liner, an intake/retention/transfer composite, a pulp and binder fiber storage layer, and a polyethylene baffle, said composite having between more than 6 and 25 weight percent superabsorbent, between 5 and 15 weight percent binder, between 0 and 40 weight percent synthetic fiber, and pulp , said composite having a density less than 0.17 g/cc, said material demonstrating fluid partitioning such than less than 72 percent of a menses simulant insult remains in said composite as measured by weight percentages of simulant in accordance with a flat system testing procedure, and further wherein said composite has a retention capacity of at least 2.7 g/g.

* * * * *